(12) United States Patent
Grader et al.

(10) Patent No.: US 10,758,495 B2
(45) Date of Patent: Sep. 1, 2020

(54) LATTICE LOSS REDUCTION

(71) Applicant: Luye Pharma AG, Miesbach (DE)

(72) Inventors: Ludwig Grader, Andernach (DE); Holger Piotrowski, Schliersee (DE)

(73) Assignee: Luye Pharma AG, Miesbach (DE)

( * ) Notice: Subject to any disclaimer, the term of this patent is extended or adjusted under 35 U.S.C. 154(b) by 240 days.

(21) Appl. No.: 14/372,268

(22) PCT Filed: Jan. 21, 2013

(86) PCT No.: PCT/EP2013/051058
§ 371 (c)(1),
(2) Date: Jul. 15, 2014

(87) PCT Pub. No.: WO2013/107909
PCT Pub. Date: Jul. 25, 2013

(65) Prior Publication Data
US 2014/0364294 A1 Dec. 11, 2014

(30) Foreign Application Priority Data
Jan. 20, 2012 (EP) .................................... 12152009

(51) Int. Cl.
*B23D 19/06* (2006.01)
*A61K 9/70* (2006.01)

(52) U.S. Cl.
CPC .......... *A61K 9/7092* (2013.01); *A61K 9/7038* (2013.01); *B23D 19/065* (2013.01)

(58) Field of Classification Search
CPC .... B23D 19/065; B31B 70/18; A61K 9/7038; A61K 9/7092

USPC .................... 83/333, 408, 687, 107
See application file for complete search history.

(56) References Cited

U.S. PATENT DOCUMENTS

| | | | | | |
|---|---|---|---|---|---|
| 1,433,138 | A | * | 10/1922 | Kruse | B23D 19/065 29/415 |
| 1,826,889 | A | * | 10/1931 | Koch | D06H 7/24 83/333 |
| 2,530,319 | A | * | 11/1950 | Young | B26D 3/10 83/333 |
| 3,517,532 | A | * | 6/1970 | Zilkowsky | B23D 19/065 72/31.07 |
| 3,762,250 | A | * | 10/1973 | Huskey | B26D 1/035 83/107 |
| 4,164,170 | A | * | 8/1979 | Nordin | B31B 19/18 383/37 |

(Continued)

FOREIGN PATENT DOCUMENTS

| | | |
|---|---|---|
| DE | 10 2008 059 054 A1 | 5/2010 |
| WO | WO 00/62763 | 10/2000 |

OTHER PUBLICATIONS

PCT/EP2013/051058—International Search Report, dated Apr. 26, 2013.

(Continued)

*Primary Examiner* — Kenneth E Peterson
(74) *Attorney, Agent, or Firm* — Curatolo Sidoti Co., LPA; Salvatore A. Sidoti; Floyd Trillis, III

(57) ABSTRACT

Methods for producing systems for the transdermal or permucosal administration of active substances and particularly transdermal therapeutic systems (TTS), wherein the active substance depots thereof have a shape that deviates from a rectangular design.

25 Claims, 7 Drawing Sheets

(56) References Cited

U.S. PATENT DOCUMENTS

Figure 1:
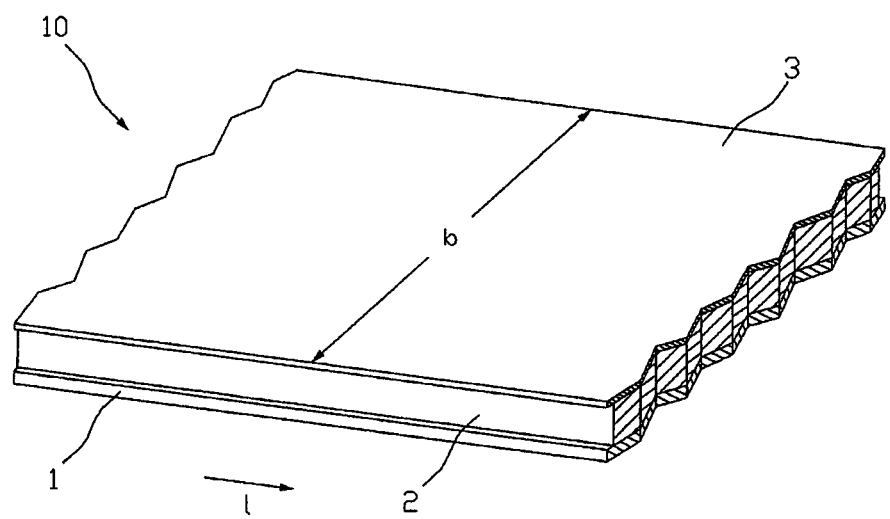

| | | | | |
|---|---|---|---|---|
| 4,368,051 A * | 1/1983 | Lehmacher | ............ | B31B 19/18 |
| | | | | 493/11 |
| 4,398,903 A * | 8/1983 | Lehmacher | ............ | B26D 1/065 |
| | | | | 493/197 |
| 4,605,392 A * | 8/1986 | Achelpohl | ............ | B31B 70/00 |
| | | | | 493/196 |
| 4,681,001 A * | 7/1987 | Uehlinger | ............ | B23D 19/065 |
| | | | | 83/300 |
| 4,846,033 A * | 7/1989 | Uehlinger | ............ | B23D 19/065 |
| | | | | 83/300 |
| 4,932,932 A * | 6/1990 | Schmidt | ............ | B26D 1/225 |
| | | | | 493/200 |
| 5,405,486 A * | 4/1995 | Sablotsky | ............ | A61F 13/0276 |
| | | | | 156/250 |
| 6,183,770 B1 | 2/2001 | Muchin et al. | | |
| 6,261,593 B1 | 7/2001 | Muchin et al. | | |
| 6,336,307 B1 * | 1/2002 | O'Connor | ............ | B65D 85/67 |
| | | | | 270/39.05 |
| 6,994,005 B2 * | 2/2006 | Lamothe | ............ | B65H 20/02 |
| | | | | 226/21 |
| 7,331,266 B2 * | 2/2008 | Chen | ............ | B26D 5/10 |
| | | | | 83/633 |
| 2008/0202675 A1 * | 8/2008 | Sever | ............ | B32B 37/025 |
| | | | | 156/238 |

OTHER PUBLICATIONS

PCT/EP2013/051058—International Written Opinion, dated Apr. 26, 2013.
PCT/EP2013/051058—International Preliminary Report on Patentability, dated Jul. 22, 2014.

* cited by examiner

LATTICE LOSS REDUCTION

CROSS REFERENCE TO RELATED APPLICATIONS

This application is a national stage application of International Application No. PCT/EP2013/051058, filed 21 Jan. 2013, which claims priority from European Patent Application No. 12152009.2, filed 20 Jan. 2012, from which applications priority is claimed, and which are incorporated herein by reference.

The present invention relates to methods for producing systems for the transdermal or permucosal administration of active substances and particularly transdermal therapeutic systems (TTS), wherein the active substance depots thereof have a shape that deviates from a rectangular design.

Usually, transdermal therapeutic systems comprise an active substance depot that on one side is overall covered by an active substance impermeable back layer and on the opposite application side by a protective film. The often multi-part protective film is removed before an application of the system to enable its attachment to the skin of a patient.

For producing transdermal therapeutic systems at first an active substance-containing coating is applied to a carrier film web, (cf. DE 10 2008 059 054 A1). The coating has a different structure depending on the type of the active substance depot to be prepared therefrom. At present, two basic types of transdermal therapeutic systems are known, matrix systems and reservoir systems. In the so-called matrix systems the active substance is contained in a polymer matrix that is often formed from a pressure sensitive adhesive (PSA). In these systems, the active substance delivery is exclusively controlled via the concentration gradient to the skin. In the so-called reservoir systems the active substance is contained in a liquid, semisolid or solid reservoir with a membrane being usually used to regulate the active substance delivery that in general is located at the application side of the active substance depot that faces the protective film.

In the further course of the production process the areas in the one- or multi-ply active substance-containing coating used to form the single active substance depots are separated for which a continuous or discontinuous pressure forming method is often employed. The web width of the carrier film used for the production generally exceeds the dimensions of the single areas required per active substance depot by several times so that for a better use of the active substance-containing coating several active substance depot areas are arranged next to each other in the transverse direction of the carrier film web. Thus, leaving aside possible rim zones of the coating layer an almost hundred percent use of the active substance-containing coating can be achieved in the active substance depots having a rectangular base area.

However, if the active substance depots to be separated or the area required per active substance depot for the course of the process do not have rectangular outlines, then the contour lines cannot be arranged adjacent to one another, whereby for the later product regions are formed that cannot be used as active substance depot. If, for example active substance depots having circular base areas are arranged next to each other such that their outer edges touch, then the loss, i.e. the proportion of the active substance-containing coating that is not used as active substance depot, by ignoring rim zones is barely 22 percent.

However, such an idealized arrangement of the active substance depots in a technical production process is practically impossible since in the further course of the method the active substance depot areas have to be separated from the areas not used as active substance depots. If the outer edges of the active substance depots touch, so between the active substance depot areas single isolated unused areas are formed that individually have to be separated from the active substance depots. Such a method would be error-prone and uneconomical, so that the area not used for active substance depots is typically removed in one piece, preferably by stripping (the so-called weeding). For that it is necessary that the lattice structure to be stripped at no point falls below a minimum width so that the lattice does not tear.

So, the unused part of the active substance-containing coating forms a continuous region called lattice and thus, in the further method can easily be stripped off from the carrier film web. If, for example, round active substance depots having diameters of 37.5 mm are arranged in a matrix type next to each other such that the shortest distance, also called lattice rib width, between two mutually adjacent active substance depots is 5 mm, then there is obtained a lattice loss, i.e. a proportion of the region of the active substance-containing coating not used by the active substance depots, of already 39% that with very expensive active substances can be expressed in very serious additional costs.

Thus, it is desired to design the production of transdermal therapeutic systems such that the use of the active substance-containing coating with non-rectangular area geometries for an active substance depot is improved.

Now, the present invention is based on the fact that corresponding active substance depot areas are arranged on a carrier film web coated with the active substance in parallel rows such that the proportion of the surface of the coated carrier film web that is not used as active substance depot area by ignoring the rim zones of the coated carrier film web is less than 39% of the total area of the coated carrier film web. Here, rim zones are defined as those regions of the coated carrier film web that in the web direction, i.e. towards the rims, are not in a line that is tangential to the active substance depot areas each forming the outer row of the active substance depot areas. Thus, these two rim zones of the coated carrier film web are not taken into account in calculating the total area of the coated carrier film web.

Thus, in this first embodiment the present invention relates to a method for producing systems for the transdermal or permucosal administration of active substances, wherein the method comprises the following steps:

providing a coated carrier film web (10) comprising a carrier film web (1) with an active substance-containing coating (2) adherent thereon, wherein active substance depot areas (12) are defined on the coated carrier film web (10) such that the active substance depot areas (12) are arranged in the web direction (l) of the coated carrier film web (10) in two or more rows such that the proportion of the surface of the coated carrier film web (10) that is not used as active substance depot area (12) by ignoring the rim zones of the coated carrier film web (10) is less than 39% of the total area of the coated carrier film web (10); and severing (S4) the coated carrier film web (10) in the web direction (l) into two or more sub-webs (15a, 15b, 15c, 15d) such that each sub-web contains a row of active substance depot areas (12).

In this method the two or more rows of the active substance depot areas are arranged on the coated carrier film web preferably in parallel rows.

In order to solve the above-described problem in removing the part of the coating not belonging to the active substance depots (blanking skeleton chad) by weeding, the present invention in another embodiment suggests to define the active substance depot areas such that the rows in the web direction cannot be separated by means of a straight line without this line falling below a distance d/2 from the active substance depot areas, wherein d is defined as the minimum distance between two active substance depot areas required for weeding.

In this second embodiment the present invention relates to a method for producing systems for the transdermal or permucosal administration of active substances, wherein the method comprises the following steps:

providing a coated carrier film web (10) comprising a carrier film web (1) with an active substance-containing coating (2) adherent thereon, wherein active substance depot areas (12) are defined on the coated carrier film web (10) such that the active substance depot areas (12) in the web direction (l) of the coated carrier film web (10) are arranged in two or more (preferably parallel) rows such that the rows in the web direction (l) cannot be separated by means of a straight line without this line falling below a distance d/2 from the active substance depot areas (12), wherein d is defined as the minimum distance between two active substance depot areas (12) required for weeding; and severing (S4) the coated carrier film web (10) in the web direction (l) into two or more sub-webs (15*a*, 15*b*, 15*c*, 15*d*) such that each sub-web contains a row of active substance depot areas (12).

The above-described method according to the second embodiment of the present invention represents an independent alternative to the first described method claimed in claim 1. However, it is preferred to combine the methods according to the first and second embodiment, so that in this case the method claimed in claim 2 depends on the method according to claim 1.

The minimum distance d of the active substance depots from each other required for weeding depends on various factors and can be determined by the skilled person for the particular case. The required width particularly depends on the material of the active substance-containing coating. The more tearproof this material is the smaller the width of the "bridges" remaining in the blanking skeleton without causing tearing of the lattice upon weeding, i.e. stripping the blanking skeleton. Other factors are the strength of the adhesion of the active substance-containing coating to the carrier film web as well as the processing speed and construction of the weeding device. Moreover, the size of the active substance depot areas has an influence on the stability of the blanking skeleton chad. In the end, all these factors as well as the resulting minimum width d of the lattice bridges can be determined by simple practical experiments by the skilled person, for example.

In practice, for example minimum distances d between two active substance depot areas of 10 mm, 9 mm, 8 mm, 7 mm, 6 mm, 5 mm, 4 mm, 3 mm, 2 mm, or 1 mm have proven to be useful.

In a third embodiment the present invention is based on the fact that corresponding active substance depot areas are arranged on a carrier film web coated with the active substance in parallel rows such that the adjacent rows overlap such that unused areas of a row of active substance depot areas of an adjacent row are at least partially occupied. However, this leads to the problem that the corresponding carrier film webs cannot as usual be cut into straight strip-like sub-webs, since in this way active substance depot areas would be cut and the thus obtained active substance depots would become useless. To solve this problem the method according to the invention of claim 3 is provided.

According to that, the present invention relates to a method for producing systems for the transdermal or permucosal administration of active substances, wherein the method comprises the following steps:

providing a coated carrier film web (10) comprising a carrier film web (1) with an active substance-containing coating (2) adherent thereon, wherein active substance depot areas (1) are defined on the coated carrier film web (10) such that these in the web direction (l) of the coated carrier film web (10) are arranged in two or more (preferably parallel) rows such that the rows in the web direction (l) cannot be separated by means of a straight line without thereby cutting active substance depot areas (12); and severing (S4) the coated carrier film web (10) in the web direction (l) into two or more sub-webs (15*a*, 15*b*, 15*c*, 15*d*) such that each sub-web contains a row of active substance depot areas (12), wherein upon severing none of the active substance depot areas (12) is cut.

Also the preceding method according to the third embodiment of the present invention can either be independent from the method of the first embodiment or contain the features of the method of the first embodiment. In the second mentioned variant, the method according to claim 3 relates to the method according to claim 1.

The method according to the invention has the advantage that severing of the coated carrier film web in the web direction into two or more sub-webs is not rectilinear, but for example is wave-like such that upon severing the coated carrier film web none of the active substance depot areas is cut. This enables an optimum utilization of the area of the coated carrier film web without intersecting active substance depot areas upon severing the carrier film web into single sub-webs so that all obtained active substance depot areas can actually be used as active substance depots.

The thus obtained sub-webs containing the active substance depot areas arranged in a row then can either separately be cut into individual regions each containing only one active substance depot or the active substance depots may individually be detached from the sub-webs and processed.

However, it is advantageous if the sub-webs obtained from a coated carrier film web could be processed in parallel. For that, the sub-webs obtained in accordance with the above-described method according to the invention however still have the drawback that the individual active substance depot areas of parallel sub-webs are present staggered in the web direction. In other words, the active substance depots on adjacent sub-webs are not exactly at the same position towards the web direction, what makes the machine processing difficult. This additional problem is solved by the preferred embodiments of the method according to the invention described in claims 4 and 5.

After this, the method according to the invention as a further step can comprise the change of the location of the sub-webs relative to each other, so that none of the sub-webs laterally engages one of the other sub-webs. The sub-webs are spaced by this processing step so that they can be more easily processed and in particular, a displacement of the sub-webs in the web direction relative to each other is made possible.

In a further preferred embodiment the method according to the invention as an additional step comprises the displacement of the sub-webs relative to each other in the web direction such that the parallel lying sub-webs in a direction 90° to the web direction can be severed in straight lines such that individual portions are obtained each containing only one active substance depot area, and wherein upon severing none of the active substance depot areas is cut. Displacing the sub-webs makes it possible to subsequently process the individual active substance depots located next to each other on parallel sub-webs in parallel in a straight line. This facilitates the further processing of a continuous processing device, for example.

In the method according to the invention the web direction generally is a direction of the longer lateral edge of the coated carrier film web. In general, respective carrier film webs have a relatively small width and a length that exceeds their width many times over. Then, the web direction extends towards the length of the carrier film web.

In the method according to the invention it is important that the active substance depot areas are neither cut in the web direction of the coated carrier film web nor crosswise thereto. That means that upon severing the coated carrier film web or even only the active substance-containing coating none of the active substance depot areas is severed. In other words, partition lines may maximally run tangentially along an active substance depot area, but not through such an area.

In a further embodiment of the method according to the invention the active substance depot areas are arranged such that the arrangement has no tetrad rotational axis, preferably such that the arrangement has the group p6m symmetry elements.

In a further preferred embodiment the method according to the invention is designed such that the proportion of the surface of the coated carrier film web that is not used as an active substance depot area by ignoring the rim zones is less than 38%, 37%, 36%, 35%, 34%, 33%, 32%, 31%, 30%, 29%, 28%, 27%, 26%, 25%, 24%, 23%, 22% or even 21% of the total area of the coated carrier film web.

The active substance depot areas may be defined by pressure forming the coated carrier films. So it is for example possible that in a coated carrier film web the active substance depot areas are at first defined by pressure forming and subsequently the other processing steps, that is severing of the carrier film web into sub-webs etc., are carried out. However, it is also possible that the active substance depot areas at first are only abstractly defined on the coated carrier film web and the actual forming of the active substance depots is carried out only after severing the coated carrier film web in two or more sub-webs for example by pressure forming the active substance depot areas or at an even later time after carrying out further other processing steps.

Also, at an arbitrary time within the method according to the invention, but preferably after obtaining the active substance depots for example by pressure forming and before severing the carrier film web in sub-webs the region of the coated carrier film web not defined as active substance depot area can be removed, for example by the so-called weeding.

In a fourth embodiment of the present invention, that in turn can be dependent on or independent of the method according to the above-described first embodiment, the method is carried out such that instead of the definition of the active substance depot areas on the coated carrier film web an arrangement of non-overlapping cell regions on the active substance-containing coating is determined, wherein the cell regions define the maximum extension of the active substance depot areas, but the active substance depot areas may also be smaller, so that they only occupy a part of the cell regions. In this definition of the invention the method is characterized in that the arrangement of the non-overlapping cell regions is selected such that the step of displacing the individual sub-webs relative to each other in the web direction without the preceding step of changing the location of the sub-webs relative to each other such that none of the sub-webs laterally engages another sub-web is not possible without overlaps of adjacent sub-webs.

Embodiments of such a production comprise a method comprising steps for providing a carrier film web with an active substance-containing coating adherent thereon, for determining an arrangement of non-overlapping cell regions on the active substance-containing coating, for severing the coated carrier film web in two or more sub-webs such that each of the partition lines exclusively separates cell regions from each other that are arranged adjacent to each other immediately crosswise to the web direction of the carrier film, for changing (S5) the location of the sub-webs relative to each other such that none of the sub-webs laterally engages one of the other sub-webs, and for displacing (S6) the individual sub-webs relative to each other in the web direction of the carrier film such that crosswise to the web direction next adjacent cell regions to each other in the web direction have no offset, wherein the arrangement of the non-overlapping cell regions is selected such that step (S6) without the preceding step (S5) is not possible without overlaps of adjacent sub-webs.

In a preferred embodiment of this method the arrangement of the non-overlapping cell regions on the active substance-containing coating is determined such that the sum of the individual transverse extensions of two cell regions arranged next adjacent in the transverse direction of the carrier film is greater than the total transverse extension of the two cell regions.

Also in this embodiment of the method according to the invention it is advantageous if the arrangement of the overlapping cell regions is selected such that this arrangement has no tetrad rotational point, particularly such that circular active substance depots can be arranged in the cell regions such that the arrangement of the circular active substance depots has the group p6m symmetry elements.

Moreover, it is also advantageous if the arrangement of the non-overlapping cell regions is selected such that circular active substance depots can be arranged in the cell regions such that the proportion of the active substance-containing coating not used as active substance depot by ignoring rim zones is less than 38%, 37%, 36%, 35%, 34%, 33%, 32%, 31%, 30%, 29%, 28%, 27%, 26%, 25%, 24%, 23%, 22% or even 21% of the total area of the coated carrier film web, with the rim zones being defined as above.

The method enables an engaging arrangement of the cell regions in the direction crosswise to the longitudinal extension of the still untreated carrier film and with that an improved use of the coating to form active substance depots for use in transdermal therapeutic systems.

Advantageously, the preparation is carried out using a device that comprises the facilities listed below. A facility designed to provide a carrier film web to which an active substance-containing coating is applied in adherent manner. A partition facility that is designed to severe the coated carrier film web in two or more sub-webs such that each partition line introduced into the carrier film web by the partition facility exclusively separates regions that are arranged adjacent to each other immediately crosswise to the web direction of the carrier film, each intended to form an active substance depot for a transdermal therapeutic system. An offset facility designed to change the location of the sub-webs relative to each other such that none of the sub-webs laterally engages one of the other sub-webs. And a balancing facility designed to displace the individual sub-webs relative to each other in the web direction of the carrier film such that crosswise to the web direction next adjacent regions of different sub-webs intended to form active substance depots have no offset to each other in the web direction.

To advantageously arrange the sub-webs uncrossed next to each other such that none of the rims of a sub-web laterally engages the rim of another sub-web changing the location of the sub-webs relative to each other in said method comprises an enlargement of the distance between the sub-webs such that the transverse extension of two cell regions arranged next adjacent on immediately adjacent sub-webs is equal or greater than the sum of the individual transverse extensions of these cell regions. To carry out such a processing step the production device preferably has a correspondingly designed offset facility. The lateral offset of the sub-webs in preferred embodiments of such offset facilities is achieved by means of swivel frames known in the prior art.

Furthermore, preferred embodiments of the method have steps for severing the active substance-containing coating along self-contained linear geometries arranged within the cell regions (=active substance depots), wherein the minimum distance of the geometries to a rim line of the cell regions corresponds to a given value of preferably less than 5 mm, and for removing the proportions of the cell regions that are not surrounded by the linear geometries. An appropriate separation of the active substance depots in the coating performed e.g. by means of pressure forming or contour punching, respectively, makes it possible to design the proportions of the coating not used as active substance depot as a contiguous lattice that can easily be stripped off.

Accordingly, advantageous embodiments of the production device further have a contouring facility designed to severe the active substance-containing coating along self-contained linear geometries, wherein the contouring facility is further designed for placing the geometries within regions intended to form active substance depots such that the minimum distance of the geometries to a rim boundary of the regions corresponds to a given value that may be for example less than 10 mm, less than 9 mm, less than 8 mm, less than 7 mm, less than 6 mm, less than 5 mm, less than 4 mm, less than 3 mm, less than 2 mm or less than 1 mm. Further preferred embodiments of the device accordingly have a weeding facility designed to remove the proportions of the regions intended to form active substance depots surrounded by the linear geometries.

Further preferred embodiments of the method provide a performance of severing the coated carrier film web into sub-webs such that in this way the location and extension of the cell regions on the active substance-containing coating is set, and thus, the division or sub-division of the coating into cell regions has advantageously been performed implicitly.

In further advantageous embodiments changing the location of the sub-webs relative to each other is performed simultaneously to the displacement of the individual sub-webs relative to each other in the web direction, for example by oblique running the sub-webs along paths varying in length.

Removal of the proportions of the cell regions not surrounded by the linear geometries in advantageous embodiments is performed after severing the active substance-containing coating along the linear geometries arranged within the cell regions, and this is after changing the location of the sub-webs relative to each other and displacing them relative to each other in the web direction.

In other preferred embodiments severing the coated carrier film web into sub-webs is performed after the removal of the proportions of the cell regions not surrounded by the linear geometries, and this is after severing the active substance-containing coating along the linear geometries arranged within the cell regions.

In also preferred embodiments the removal of the proportions of the cell regions not surrounded by the linear geometries is performed after changing the location of the sub-webs relative to each other and displacing them relative to each other in the web direction, and the latter after severing the active substance-containing coating along the linear geometries and severing the coated carrier film web in sub-webs.

The described embodiments allow an effective use of the active substance-containing coating especially with not rectangular designed active substance depots, so that in preferred embodiments of the method the self-contained linear geometries are circular or elliptical.

Figure 2:
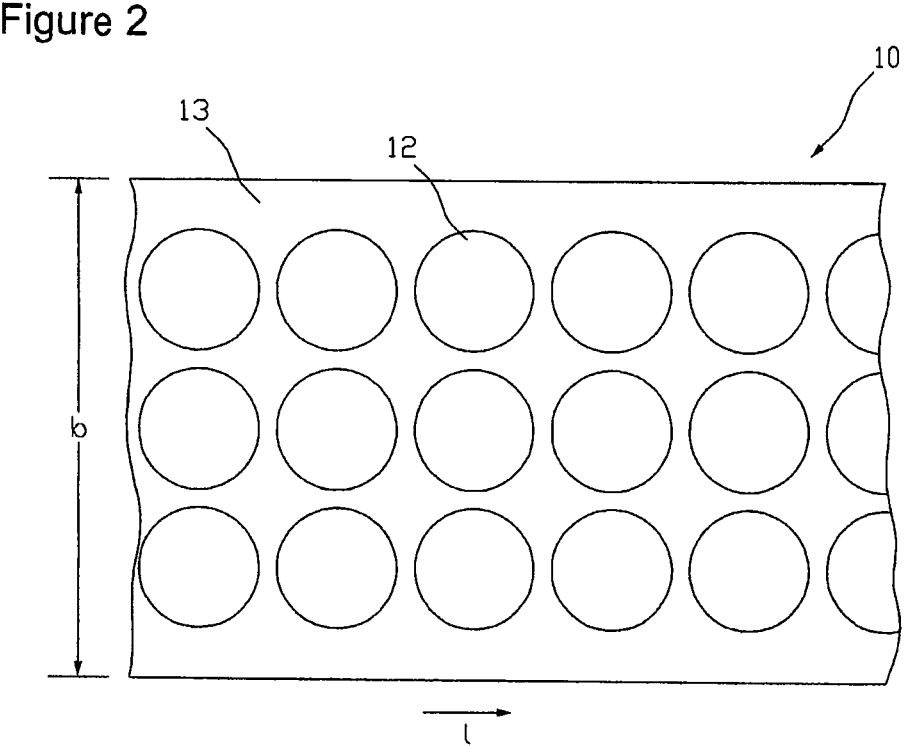
Figure 3:
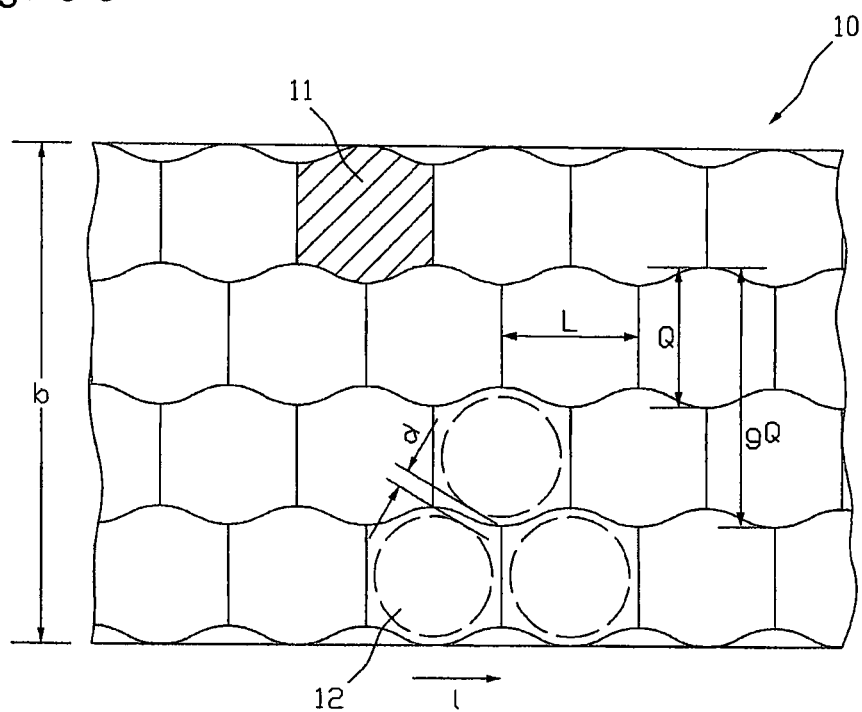
Figure 4:
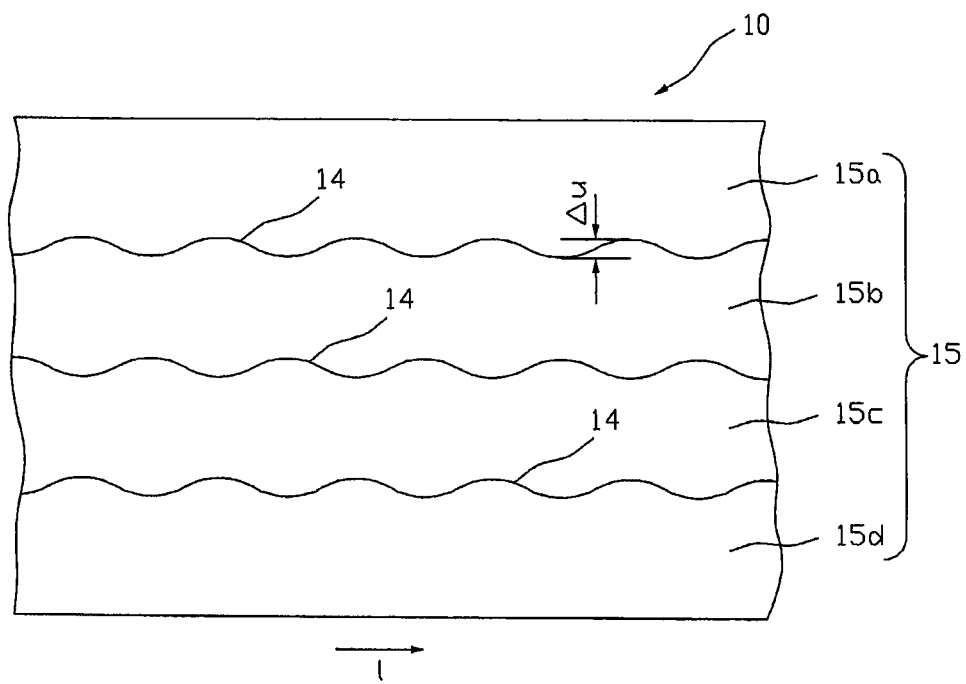
Figure 5:
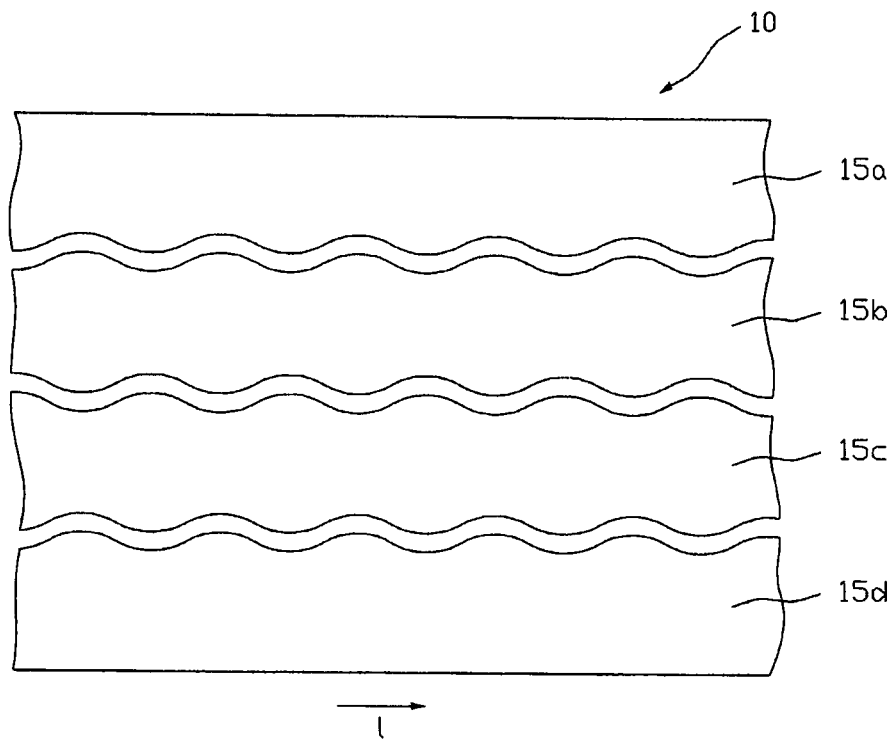
Figure 6:
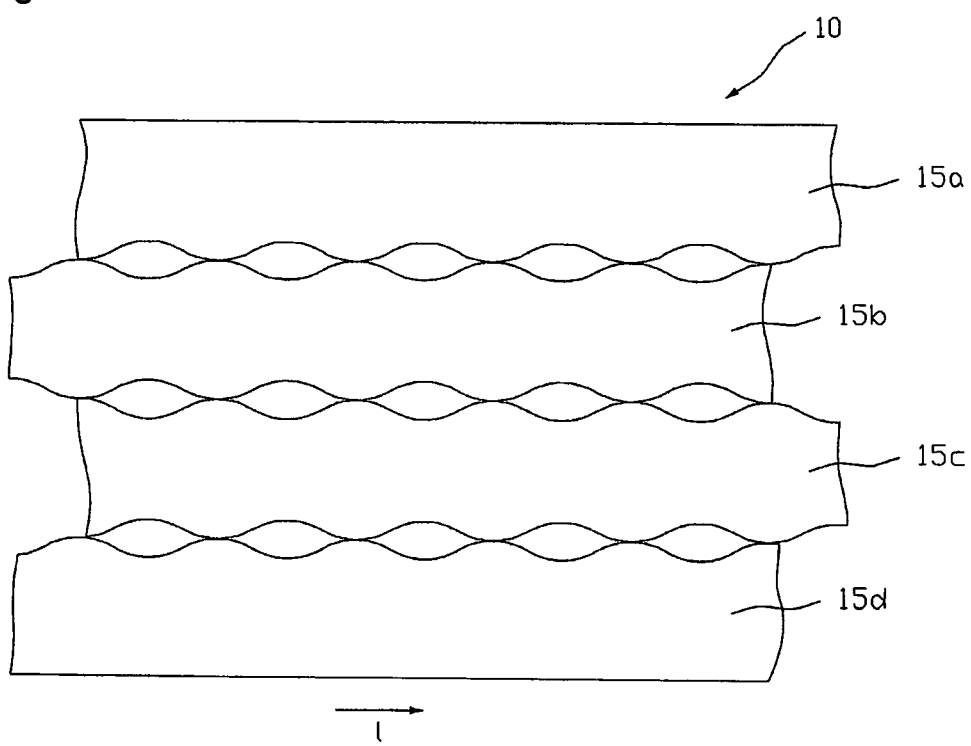
Figure 7:
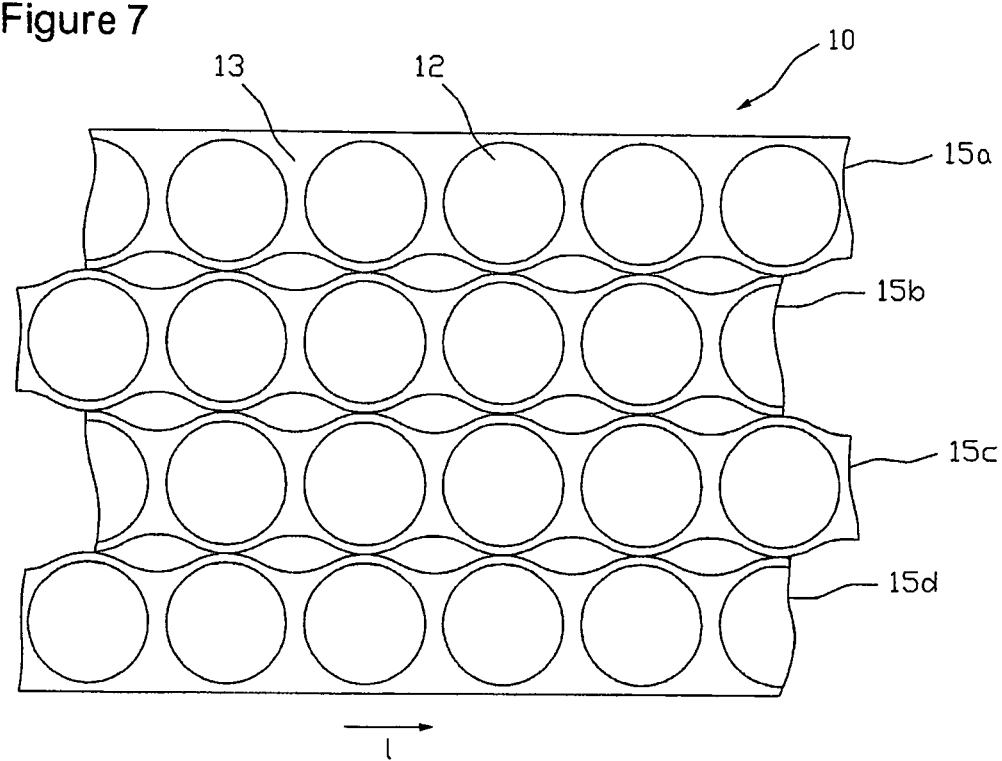
Figure 8:
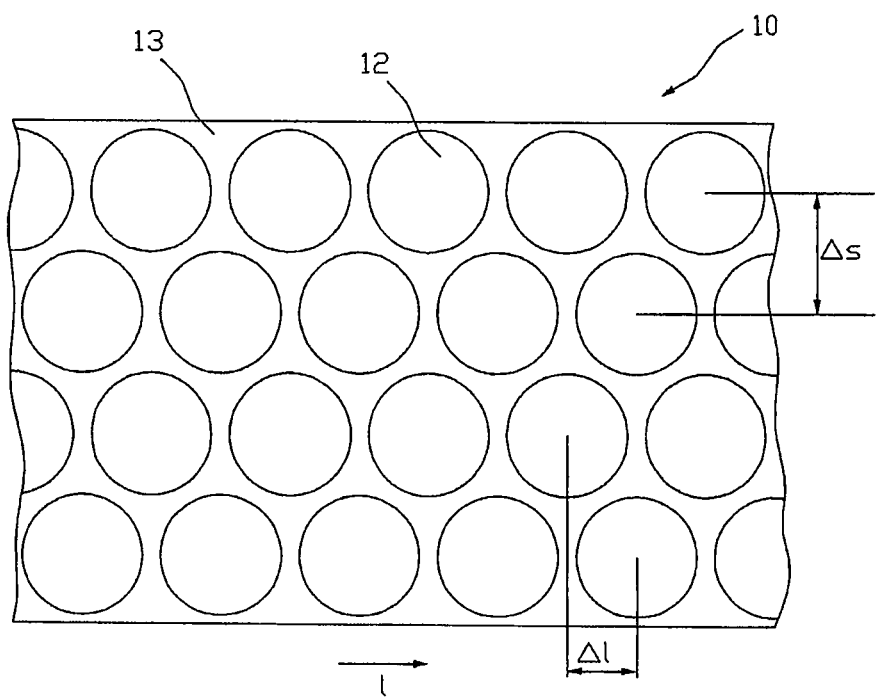
Figure 9:
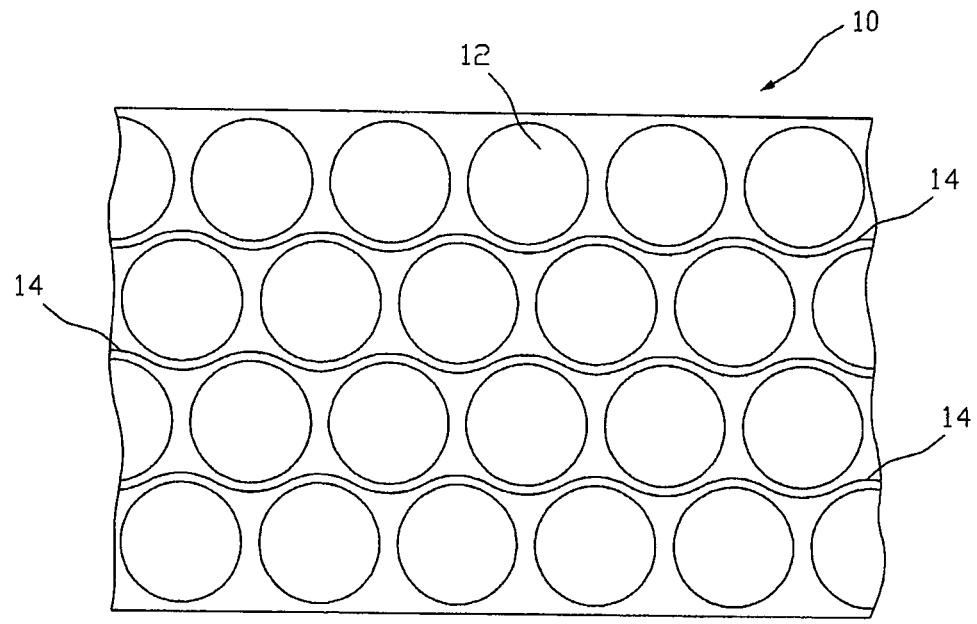
Figure 10:
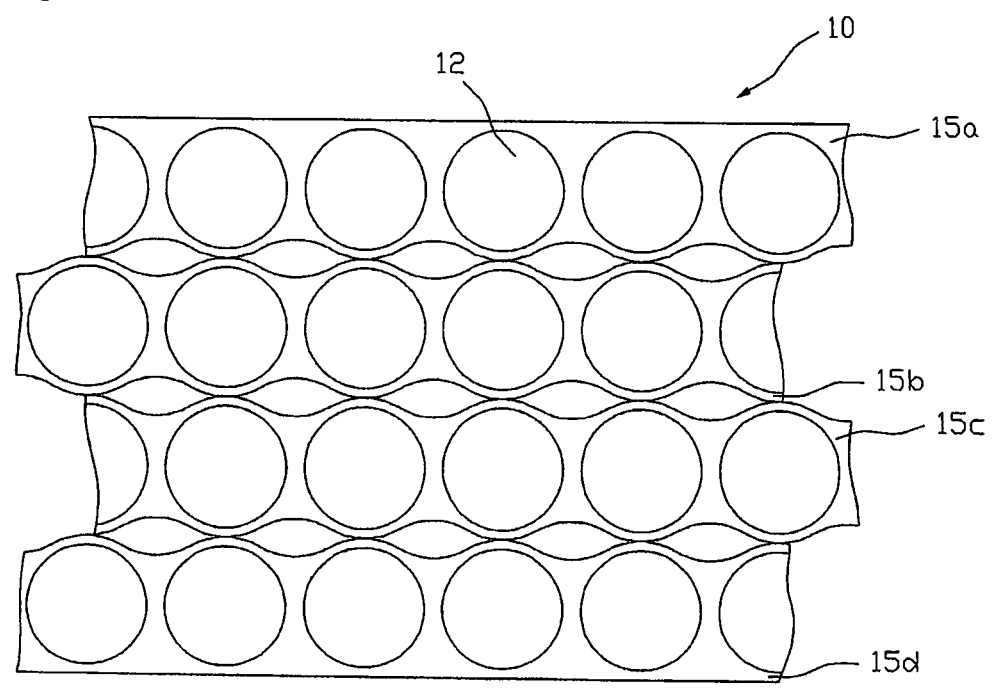
Figure 11:
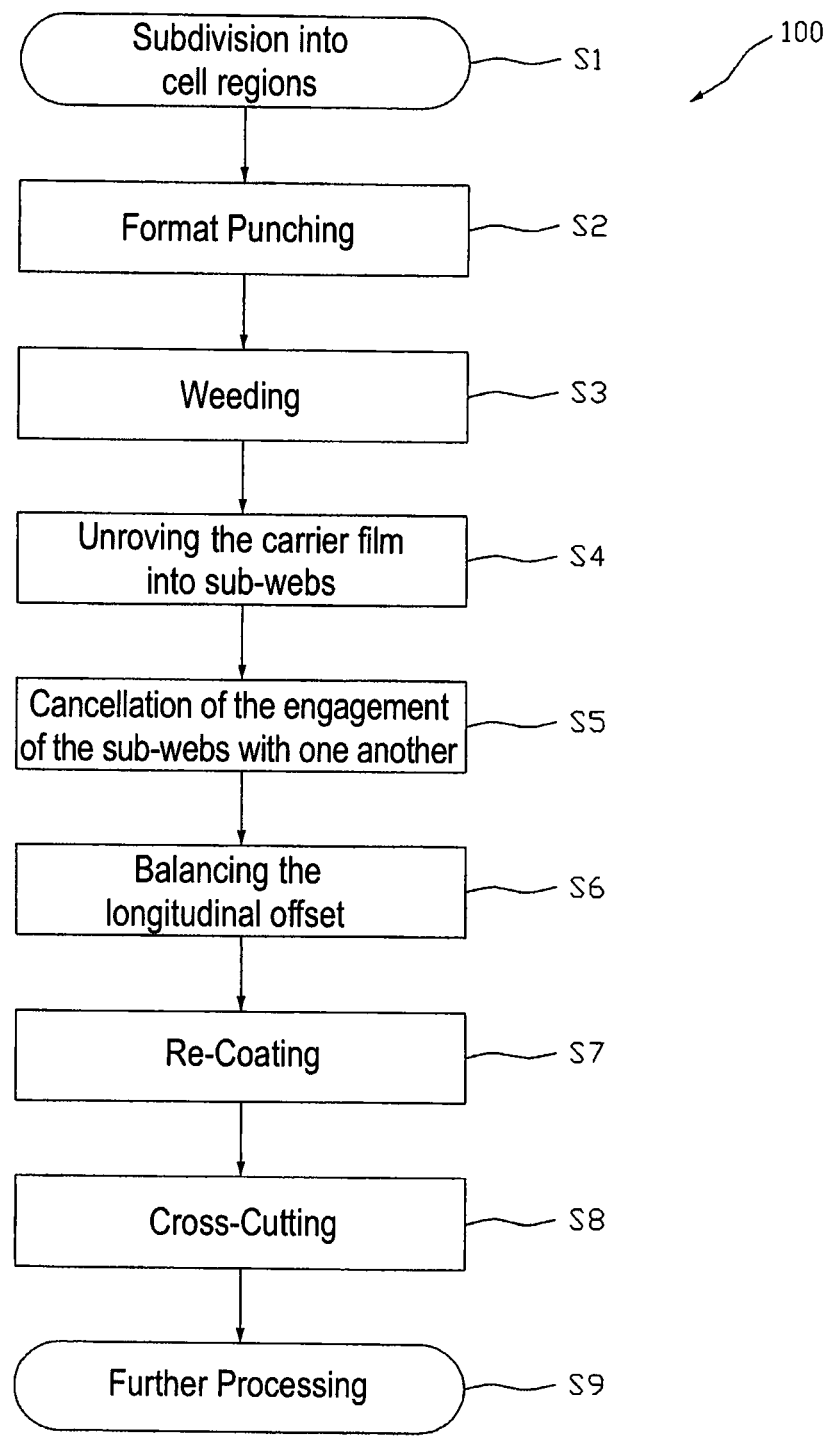
Figure 12:
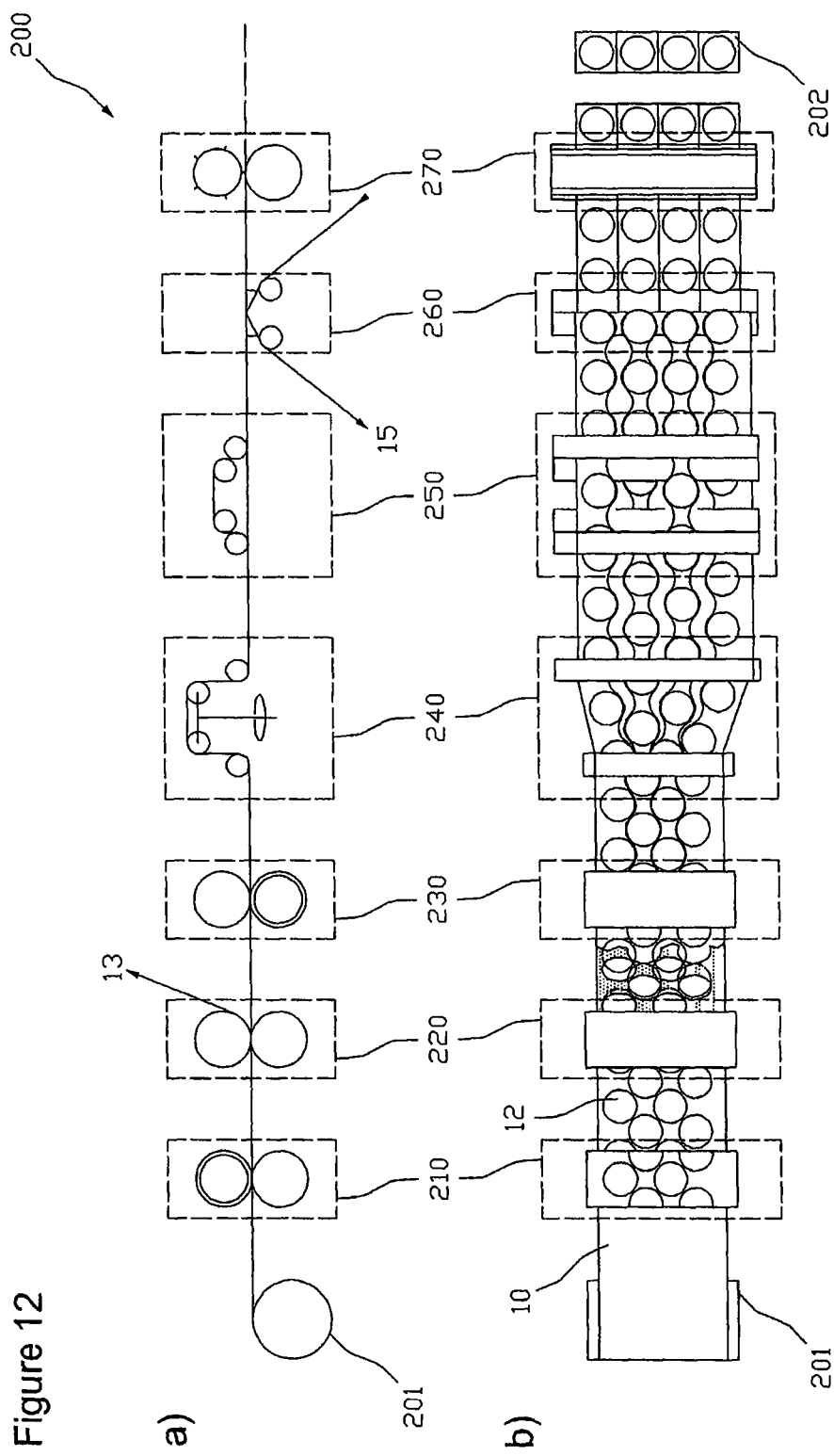

Further features of the invention result from the following description of examples in conjunction with the claims as well as the enclosed figures. It should be noticed that the invention is not limited to the embodiments of the described examples, but is defined by the scope of the enclosed claims. In particular, in the embodiments according to the invention the features cited in the examples discussed below may be realized in a number and combination differing from the examples. In the following discussion of some examples of the invention reference is made to the enclosed figures. Here, FIG. 1 shows the structure of a coated carrier film web for producing transdermal therapeutic systems in a schematic view, FIG. 2 in a schematized top view illustrates a coated carrier film web with active substance depots for transdermal therapeutic systems separated thereon in a conventional manner, FIG. 3 shows a top view onto the coated carrier film web with a graphic emphasis of an arrangement of adjacent element cells in a schematized view, FIG. 4 shows an arrangement of partition lines for unroving the coated carrier film web of FIG. 3 into sub-webs in a schematized view, FIG. 5 shows a schematic view of a carrier film web unroved along the partition lines of FIG. 4, the thus generated sub-webs of which have been laterally spaced, FIG. 6 shows a schematic top view onto a carrier film with sub-webs displaced relative to each other by a longitudinal offset between active substance depots or cell regions, respectively, of adjacent rows, FIG. 7 schematically illustrates the separation of active substance depots on the active substance-containing coatings of the sub-webs, FIG. 8 shows an example of a space-using separation of round active substance depots on a coated carrier film in a schematic view, FIG. 9 schematically illustrates the coated carrier film of FIG. 8 unroved into sub-webs, FIG. 10 represents a schematic illustration of the sub-webs of FIG. 9 after lateral spacing, longitudinal offset balancing, and weeding, FIG. 11 illustrates an embodiment of a method for better use of the active substance-containing coating in the form of a flow chart; and FIG. 12 illustrates a device for producing transdermal therapeutic systems with improved active substance utilization in a function-schematized side view and top view.

In the figures same or similar reference numbers for functionally equivalent or similar characteristics are independently used by specific embodiments.

FIG. 1 illustrates the structure of a coated carrier film web 10 for producing transdermal therapeutic systems. For better clarification of the facts the illustration is not true to scale. The coated carrier film web 10, of which only a section is shown in FIG. 1, has a certain width b and a much greater length l relative to the width. The coated carrier film web 10 consists of at least two layers, the carrier film web 1 and an active substance-containing coating 2 applied thereon. Typically, the side of the active substance-containing coating 2 turned away from the carrier film web 1, as shown in the example illustrated in FIG. 1, is additionally covered by a covering film 3 applied thereon. Depending on the particular application the active substance-containing coating 2 extends over the entire width b of the carrier film web, as shown in FIG. 1 only over a part of its width, or is applied to the carrier film 1 in the form of several single webs arranged side by side. For the purposes of an improved utilization of the active substance-containing coating 2 as described in the following this extends over the entire width b of the carrier film web 1 or at least almost over the entire width b of the carrier film web 1. According to the type of the transdermal therapeutic systems to be made of the coated carrier film web 10 the active substance-containing coating 2 may be constructed of one or more layers and also comprise a membrane.

Besides the transdermal therapeutic system to be prepared the width of the coated carrier film web 10 first of all depends on the conditions of the apparatus used for production. The web widths used often are several times the widths of the transdermal therapeutic systems to be prepared of it. To take better advantage of the coated carrier film web separation of the active substance depots 12 in the active substance-containing coating 2 is thus generally carried out in an arrangement comprising several rows. Such a matrix type arrangement of active substance depots 12 is illustrated in FIG. 2. The individual active substance depots 12, of which in the figure only one representative of all is provided with a reference number, in the illustrated arrangement are arranged in three rows. The rows extending in the longitudinal direction of the coated carrier film web 10 are arranged side by side with respect to the width of the film web 10. The adjacent active substance depots of different rows have no offset to each other in the longitudinal direction of the carrier film web 10, but are substantially at the same longitudinal position of the coated carrier film web 10. In other words, the arrangement of the active substance depots 12 corresponds to a field arrangement made up of rows and columns that is a prerequisite for the batchwise transfer of all active substance depots 12 present at the same longitudinal position of the film web 10 to a protective film or for the batchwise separation of the film web into individual portions in the course of separation of the individual transdermal therapeutic systems, respectively. By a batchwise treatment of the active substance depots herein is meant a simultaneous treatment of active substance depots lying next to each other in a column of the field arrangement.

The active substance depots 12 both are spaced to one another in the longitudinal direction of the coated carrier film web 10 and crosswise thereto, so that a contiguous lattice 13 is obtained that can easily be stripped off from the carrier film.

The above-described matrix type arrangement of the active substance depots 12 made up of rows and columns with not rectangular active substance depot geometries results in less utilization of the active substance-containing coating 2. An arrangement with an improved utilization of the active substance-containing coating 2 is represented in FIG. 8. Here, the round active substance depots 12 of adjacent rows with respect to the longitudinal direction l of the coated carrier film web 10 are staggered to each other, with the rows engaging one another such that the space available between two adjacent active substance depots 12 of a row is also used by an active substance depot 12 of a row that is immediately arranged adjacent to this row. In other words, the distance of active substance depots 12 adjacently arranged crosswise to the longitudinal extension of the carrier film 10, in the following referred to as row distance Δs, with the same lattice rib width is smaller than in an arrangement according to FIG. 2.

However, the longitudinal offset Δl between active substance depots 12 of adjacent rows hinders a columnar batchwise further processing as described above. So that the active substance depots 12 of the individual rows are arranged on the same level for further processing, i.e. without longitudinal offset, the coated carrier film web 10 is unroved into several sub-webs, wherein each of the sub-webs contains a row of areas each, intended for active substance depots 12. Subsequently, the relative position of the sub-webs to one another is changed such that the areas of different sub-webs intended for active substance depots 12 in the transverse direction are arranged next to each other without longitudinal offset Δl and without engagement Δu (see, FIG. 4).

A first method for a better utilization of the active substance-containing coating 2 by active substance depots 12 is discussed in the following with respect to FIGS. 3 to 7. In a first step of the method the active substance-containing coating 2 of width b is divided into several, preferably congruent cell regions 11. In FIG. 3, one of the cell regions is provided with a reference number representative for all and hatched for better recognition of its geometry. The individual cell regions 11 immediately adjoin to one another without intermediate regions and do not overlap.

Size and shape of a cell region 11 depend on the size and shape of the active substance depots 12 to be prepared each and on the region required for stripping off the blanking skeleton or for the projection of the later part of the release liner representing the supporting material of the individual active substance depots. The cell regions 11 shown in FIG. 3 are designed for circular active substance depots 12 the intended location of which in three of the cell regions 11 is indicated by broken lines. Under the given conditions, the determination of the shape and arrangement of the cell regions is preferably done in view of a densest possible arrangement of the areas intended to form the active substance depots on the active substance-containing coating 2. In the example shown in FIG. 3 the shape of the cell regions has been developed for an optimum utilization of the active substance-containing coating 2 by preserving a minimum distance d (lattice rib width) between immediately adjacent active substance regions 12.

Of course, with other shapes of active substance depots 12 to be prepared there result cell regions with boundary geometries deviating from that shown in FIG. 3. Moreover, the active substance-containing coating 2, in case that differently sized or not similarly shaped active substance depots 12 are to be prepared in a production process, can be divided into an arrangement of differently sized and also differently shaped cell regions 11.

With non-rectangular active substance depot geometries an optimum utilization of the active substance-containing coating 2 always exists when an active substance depot area 12 of a row is arranged near the space between two active substance depot areas 12 of a next adjacent row or engaging this space. Accordingly, a space-utilizing shape and arrangement of cell regions 11 may be characterized such that as illustrated in FIG. 3 the sum of the individual transverse extensions Q of two cell regions 11 arranged next to each other in the transverse direction of the carrier film 10 is greater than the entire transverse extension gQ of these two cell regions.

The described determination of an arrangement of non-overlapping cell regions 11 on the active substance-containing coating 2 is of pure organizational nature and is typically not reflected in an actual marking or structuring of the active substance-containing coating 2. However, it is a basis for and indirectly results from, respectively, the arrangement of the partition lines along which the coated carrier film web 10 is unroved into several sub-webs. Thus, the described first step of the method is an organizational step reflecting in the production steps described below that change the physical design of the coated carrier film web 10, but does not itself form such a production step.

FIG. 4 shows an embodiment of an arrangement of partition lines 14 for unroving the coated carrier film web 10 into four sub-webs 15a, 15b, 15c and 15d, each of which exactly contains one row of the cell regions 11 represented in FIG. 3. The partition lines are formed wave-like in accordance with the active substance depot and cell region arrangement of FIG. 3, respectively, wherein the distance Δu between two sequential inverse points of the wavy lines indicates the engagement of two sub-webs 15 engaging at the respective wavy lines. Unroving the carrier film web 10 along the partition lines 14 that forms the second step of the above-mentioned method is carried out with a cutting or punching facility (not shown in the figures). Here, unroving can be done discontinuously with a contour punch, for example, or continuously with a contour slitting roller, for example.

FIG. 5 illustrates the carrier film web 10 unroved along partition lines 14 into sub-webs 15a, 15b, 15c and 15d, wherein the individual sub-webs after unroving have additionally been laterally lead apart so far that adjacent rows do no longer engage one another, i.e. Δu=0, wherein the distance between the rows may optionally be selected greater. With that it is ensured that the individual sub-webs upon displacement of individual sub-webs for balancing the longitudinal offset Δl that is carried out in the subsequent step at best touch at certain points, but cannot partially cover each other. Alternatively, for the lateral offset of the sub-webs in embodiments for the elimination of the engagement also every second sub-web can be transferred to another level. To eliminate the longitudinal offset between active substance depots 12 or cell regions 11 of adjacent rows, respectively, every second sub-web is offset or displaced, respectively, relative to the others by a drift corresponding to the longitudinal offset Δl. For example, in a tetrad arrangement, as illustrated in FIG. 6, rim sub-web 15a and the sub-web 15c, which is the second after the rim sub-web 15a, may be displaced relative to the other two sub-webs 15b and 15d by a drift corresponding to the longitudinal offset Δl in the longitudinal direction l of the carrier film web 10. The displacement can be realized in a production plant for example by running stretches of the sub-webs different in length.

In the step following the longitudinal offset balancing the individual sub-webs of the active substance-containing coating 2 can be re-coated to a new carrier film, preferably to a protective film. Here, each of the protective films assigned to a sub-web can be formed in several parts, by which is meant that it is constructed of several sub-webs of which at least two adjoin or overlap each other such that they form a closed area. Here, the partition line between the two protective film parts or their overlapping region, respectively, is preferably arranged such that it is covered by the areas intended to form the active substance depots 12.

In the following step the active substance depots 12 in the active substance-containing coating sub-webs are separated. This is done by means of severing the active substance-containing coating 2 along self-contained linear geometries, with each of these geometries in each case is arranged in a field of the coating 2 assigned to a cell region 11. Since the active substance depots 12 have particular contours or formats, respectively, this step is also referred to as contour or format punching.

Finally, the lattices 13 are stripped off from the coating sub-webs in an operation generally referred to as weeding. If a one-part protective film was used in the preceding re-coating of the coating sub-webs this is transferred into a multi-part protective film after weeding by longitudinal cutting, wherein the protective film hereby on the one hand is severed into several sub-webs each bearing a row of active substance depots and on the other hand each of these sub-webs can be provided with a cut or perforation running along below the active substance depots 12. In a subsequent processing step the protective film webs are severed in the regions between the active substance depots in the transverse direction to obtain single systems. Further facultative processing steps may optionally comprise the covering of the active substance depots 12 with an active substance-impermeable cover or back layer film, respectively, and the package of the single systems.

The order of the above-described process steps is not stipulated and can be changed for adaption to special features of a plant for producing transdermal therapeutic systems or for other considerations, such as for example material savings, minimization of contamination and the like.

For example, for better utilization of the active substance-containing coating the above-described method may also be carried out in an order of the process steps in which after the (at least mentally) carried out step of subdividing the carrier film 10 into single cell regions 11 at first format punching for separation of the active substance depots 12 is performed, as e.g. illustrated in FIG. 8. Thereafter, the lattice 13 can be removed from the carrier film 1, whereupon unroving the carrier film 10 along partition lines 14 defined by the cell region arrangement, illustrated in FIG. 9, is done. In the following, the individual sub-webs are laterally spaced (i.e. crosswise to the longitudinal direction 1 of the carrier film web 10) and the longitudinal offset between immediately adjacent sub-webs is balanced, so that e.g. an arrangement of the format-punched sub-webs 15a, 15b, 15c and 15d in accordance with the schematic view of FIG. 10 is obtained. After longitudinal offset balancing the punched coating sub-webs are re-coated on a protective film, before this is severed by longitudinal cutting or lengthwise punching into the above-described, possibly multi-part sub-webs. Finally, also in this method sequence the protective film sub-webs are cross-cut for separation of the systems, as described above.

In a further exemplary method sequence the sub-webs at first are displaced relative to each other after unroving the carrier film web as in the above-discussed first example for cancel-ling the engagement Δu and longitudinal offset Δl, before the thus produced coating sub-webs each are transferred to an optionally multi-part protective film web. Subsequently, the active substance depots are formed by contour punching the re-coated coating sub-webs, and the parts of the coating sub-webs not used as active substance depot are weeded before separation of the systems by cross-cutting the protective film.

The flow chart of FIG. 11 shows a clear representation of the single steps of a method 100 for a better utilization of the active substance-containing coating 2 according to the method sequence referred to as the second. Method 100 in step S1 starts with the subdivision of the carrier film 10 into single cell regions 11 each of which is assigned to a single active substance depot format 12. It should again be noted that this step exclusively is of conceptual nature and does not or must not, respectively, include a physical change of the coated carrier film 10. In step S2 there is performed format punching to form the single active substance depots 12 in the coating layer 2 and optionally in the coating layer 2 provided with a covering film 3, respectively. In the following step S3 the part 13 of the active substance-containing coating layer 2 possibly coated with a covering film 3 that is not used for active substance depots 12 is weeded. After step S3, in step S4, the carrier film 10 bearing active substance depots 12 is unroved along the partition lines 14 into single sub-webs, for example in sub-webs 15a, 15b, 15c and 15d. In the following step S5 the engagement of the sub-webs is cancelled and subsequently or at the same time in step S6 the longitudinal offset between the sub-webs is balanced, whereupon cell regions 11 arranged next to each other crosswise to the longitudinal direction of the sub-webs are arranged on the same level, i.e. without longitudinal offset to one another. Cancellation of the engagement Δu or the engagement of the sub-webs with each other, respectively, can be achieved by an enlargement of the distance between the sub-webs crosswise to the longitudinal extension of the sub-webs and also transferring of each second sub-web to another level. In the latter case in the later stages (step S7) the active substance depots are re-coated on separate protective film webs. Cancellation of the longitudinal offset between the sub-webs bearing active substance depots may be realized by passing adjacent sub-webs over stretches varying in length. In step S7 the active substance depots 12 of the individual sub-webs are re-coated on one or more protective film webs or one or more other carrier film webs. In a step S8 taking place later the possibly multi-part protective films are cross-cut for separation of the systems and in step S9 the systems are transferred to their further processing.

Method 100 may be carried out in the described sequence of process steps, but also in another useful sequence of process steps as described above or otherwise deviating therefrom. So it is possible, for example in the procedure shown in FIG. 11 to ignore steps S7 and S8. Alternatively, it is possible to recover the desired product for further processing from the sub-webs after step S6 directly by cross-cutting without the intermediate step S7 shown in FIG. 11. Accordingly, processing steps after step S6 can freely be chosen by the skilled person in accordance with the respective requirements and objectives.

The described production method enables a better utilization of an active substance-containing coating applied to a carrier film for producing transdermal therapeutic systems, wherein the device components required for the realization of the method can be integrated into existing plants for producing transdermal or similar systems for the administration of transdermal or permucosal active substances. The described production method can also easily be adapted e.g. to the production of orodispersible tablets (ODT) that are often round in shape.

In the function-schematized illustrations of FIG. 12 there are schematically shown the facilities of a device 200 for producing transdermal therapeutic systems that are essential for carrying out a method as described above. Illustration a) shows the facilities in a side elevational view and illustration b) in a top view. The shown arrangement of the facilities relative to each other is selected with respect to the course of procedure illustrated in FIG. 11 and can vary in accordance with correspondingly different selected courses of procedure. In the figure, the facilities described below each are emphasized with a broken frame for better recognition.

The device 200 comprises a contouring facility 210 for separation of active substance depots 12 in the coating layer 2 that is optionally provided with a cover layer 3 by means of format or contour punching, respectively, a weeding facility 220 for removing the part of the coating layer 2 optionally provided with a cover layer 3 that is usually referred to as lattice and is not used as active substance depot 12 from the carrier film web 1, and a separating facility 230 for lengthwise unroving the carrier film web 1 into two or more sub-webs 15. To cancel an engagement Δu of the sub-webs 15 into each other the offset facility 240 can comprise swivel frames as illustrated, that laterally, i.e. crosswise to their longitudinal or transportation direction, lead the individual sub-webs 15 appropriately far apart. Other embodiments of an offset facility 240 pass adjacent sub-webs 15 over different rollers that are arranged such that adjacent sub-webs 15 are passed to different levels. In the balancing facility 250 adjacent sub-webs 15 are passed over stretches of different lengths, with the differences in the stretches substantially corresponding to the original longitudinal offset Δl of the active substance depots 12 of adjacent sub-webs 15. In the re-coating-facility 260 the active substance depots 12 are re-coated on an optionally multi-part protective film as described above. Particularly, when using an offset facility 240 transferring the sub-webs into different levels without laterally leading them apart, the re-coating-facility 260 is designed for supplying a number of optionally multi-part protective films, that corresponds to the sub-webs 15, to the sub-webs passed in different levels. For separation of the protective film web(s) bearing active substance depots 12 into single transdermal therapeutic or other systems 202 for the percutaneous administration of active substances the device 200 finally has a cross-cutting facility 270 designed to sever the protective film that previously had optionally been divided into several webs with a lengthwise cutting facility (not shown) crosswise to the longitudinal direction in the regions between the active substance depots 12. The described facilities are supplied with the coated carrier film web 10 preferably via a winding roll 201.

In a preferred embodiment the contouring facility 210 is or includes a punching device with punching blades that in some cases are firmly connected (i.e. unchangeable) with the punching device. The punching blades of the punching device are attached such that this in format punching in step S2 results in the above-described arrangement of active substance depots 12 with optimized space use. So, the punching blades may particularly be attached such that the arrangement shown in FIG. 8 is obtained. The arrangement of active substance depots 12 shown in FIG. 8 has a given row distance Δs as well as a given longitudinal offset Δl each being greater than zero. The row distance Δs and the longitudinal offset Δl are chosen such that the use of the active substance-containing coating is improved over the matrix type arrangement shown in FIG. 2. That is, the improvement is achieved by a reduction of the proportion of the region of the active substance-containing coating that is not used by the active substance depots, i.e. by a reduction of lattice loss.

In a preferred embodiment the contouring facility 210 is or includes a punching roller with firmly attached punching blades, with the punching blades being arranged such that the lattice loss is reduced. Typically, the punching blades are arranged such that the arrangement of active substance depots (12) formed by format punching in step (S2) has a given row distance Δs and a given longitudinal offset Δl each being greater than zero and each being chosen such that the lattice loss is reduced.

The punching blades of the punching device can be arranged such that when using the punching device in the format punching in step (S2) preferably round or oval active substance depots (12) are formed that are arranged in rows, with the rows engaging with one another such that the space available between two adjacent active substance depots 12 of a row is also used by an active substance depot 12 of a row that is immediately arranged adjacent to this row.

The invention claimed is:

1. A method for producing systems for the transdermal or permucosal administration of active substances, wherein the method comprises the following steps:
providing a coated carrier film web (10) comprising a carrier film web (1) with an active substance-containing coating (2) adherent thereon, wherein active substance depot areas (12) are defined on the coated carrier film web (10) such that the active substance depot areas (12) are arranged in the web direction (l) of the coated carrier film web (10) in two or more rows such that the proportion of the surface of the coated carrier film web (10) that is not used as active substance depot area (12) by ignoring the rim zones of the coated carrier film web (10) is less than 39% of the total area of the coated carrier film web (10); wherein the active substance depot areas (12) are defined such that the rows in the web direction (l) cannot be separated by means of a straight line without thereby cutting active substance depot areas (12);
forming active substance depots by cutting (S2) the active substance-containing coating (2), followed by:
severing (S4) the coated carrier film web (10) in the web direction (l) into two or more sub-webs (15a, 15b, 15c, 15d) such that each sub-web contains a row of active substance depots; wherein upon severing none of the active substance depots is cut;
displacing (S6) the sub-webs (15a, 15b, 15c, 15d) relative to each other in the web direction (l) such that the parallel lying sub-webs in a direction 90° to the web direction (l) can be severed in straight lines such that individual portions are obtained each containing only one active substance depot and wherein upon severing none of the active substance depots is cut; and
severing the sub-webs in straight lines such that individual portions are obtained each containing only one active substance depot.

2. The method according to claim 1, wherein the active substance depot areas (12) are defined such that the rows in the web direction (l) cannot be separated by means of a straight line without this line falling below a distance d/2 from the active substance depot areas (12), wherein d is defined as the minimum distance between two active substance depot areas (12) required for weeding.

3. The method according to claim 1, wherein the active substance depots or active substance depot areas, respectively, are circular or elliptical.

4. The method according to claim 1, wherein the method comprises the further step:
changing (S5) the location of the sub-webs (15a, 15b, 15c, 15d) relative to each other such that none of the sub-webs laterally engages one of the other sub-webs.

5. The method according to claim 1, wherein the active substance depots or active substance depot areas, respectively, are all equal in size.

6. The method according to claim 1, wherein the active substance depot areas (12) are arranged such that the arrangement has no tetrad rotational axis.

7. The method according to claim 1, wherein the proportion of the surface of the coated carrier film web (10) that is not used as an active substance depot area by ignoring the rim zones is less than 21% of the total area of the coated carrier film web (10).

8. The method according to claim 1, wherein the active substance depot areas (12) are defined by pressure forming (S2) of the coated carrier film web (10).

9. The method according to claim 1, wherein the method comprises the following further step:
removing (S3) the regions of the coated carrier film web (10) that are not defined as active substance depot areas (12).

10. The method according to claim 1, wherein the method comprises the following steps:
determining an arrangement (S1) of non-overlapping cell regions (11) on the active substance-containing coating (2),
wherein said two or more sub-webs (15a, 15b, 15c, 15d) comprise partition lines and said coated carried film web (10) is severed into said sub-webs such that each of the partition lines (14) exclusively separates cell regions (11) from each other that are arranged adjacent to each other immediately crosswise to the web direction of the carrier film,
changing (S5) the location of the sub-webs (15a, 15b, 15c, 15d) relative to each other such that none of the sub-webs laterally engages one of the other sub-webs, and
displacing (S6) is carried out such that crosswise to the web direction next adjacent cell regions to each other in the web direction have no offset,
characterized in that the arrangement of the non-overlapping cell regions (11) is selected such that step (S6) without the preceding step (S5) is not possible without overlaps of adjacent sub-webs.

11. The method according to claim 10, wherein the arrangement of the non-overlapping cell regions (11) is selected such that the arrangement has no tetrad rotational point.

12. The method according to claim 10, wherein the arrangement of the non-overlapping cell regions (11) is selected such that circular active substance depots can be arranged in the cell regions (11) such that the arrangement of the circular active substance depots has the group p6m symmetry elements.

13. The method according to claim 10, wherein the arrangement of the non-overlapping cell regions (11) is selected such that circular active substance depots can be arranged in the cell regions (11) such that the proportion of the active substance-containing coating not used as active substance depot by ignoring rim zones is less than 21% of the total area of the coated carrier film web (10).

14. The method according to claim 10, wherein the arrangement of the non-overlapping cell regions (11) is selected such that the sum of the individual transverse extensions (Q) of two cell regions 11 arranged next adjacent in the transverse direction of the carrier film is greater than the entire transverse extension (gQ) of these two cell regions.

15. The method according to claim 10, wherein changing (S5) the location of the sub-webs (15a, 15b, 15c, 15d) relative to each other comprises an enlargement of the distance between the sub-webs such that the transverse extension of two cell regions arranged next adjacent on immediately adjacent sub-webs is equal or greater than the sum of the individual transverse extensions of these cell regions.

16. The method according to claim 10, further comprising the following steps:
removing (S3) the proportions (13) of the cell regions (11) that are not surrounded by the active substance depots.

17. The method according to claim 16, wherein the removal (S3) of the proportions of the cell regions not forming the active substance depots is performed after changing (S5) the location of the sub-webs (15a, 15b, 15c, 15d) relative to each other and displacing (S6) them relative to each other in the web direction, and this is after severing (S2) the active substance-containing coating and severing (S4) the coated carrier film web into sub-webs.

18. The method according to claim 16, wherein severing (S4) the coated carrier film web (10) into sub-webs (15a, 15b, 15c, 15d) is performed after the removal (S3) of the proportions (13) of the cell regions (11) not forming the active substance depots, and this is after severing (S2) the active substance-containing coating.

19. The method according to claim 16, wherein the removal (S3) of the proportions (13) of the cell regions (11) not forming the active substance depots is performed after severing (S2) the active substance-containing coating (2) and this is after changing (S5) the location of the sub-webs (15a, 15b, 15c, 15d) relative to each other and displacing (S6) them relative to each other in the web direction (l).

20. The method according to claim 10, wherein severing (S4) the coated carrier film web (10) into sub-webs (15a, 15b, 15c, 15d) is performed such that in this way the location and extension of the cell regions (11) on the active substance-containing coating is set.

21. A device for producing systems for the transdermal or permucosal administration of active substances from a coated carrier film web (10) comprising a carrier film web (1) with an active substance-containing floating (2) adherent thereon, wherein active substance depot areas (12) are defined on the coated carrier film web (10) such that the active substance depot areas (12) are arranged in the web direction (l) of the coated carrier film web (10) in two or more rows such that the proportion of the surface of the coated carrier film web (10) that is not used as active substance depot area (12) by ignoring the rim zones of the coated carrier film web (10) is less than 39% of the total area of the coated carrier film web (10); wherein the active substance depot areas (12) are defined such that the rows in the web direction (l) cannot be separated by means of a straight line without thereby cutting active substance depot areas (12); the system comprising:
a contouring facility (210) which is for severing the active substance-containing coating (2) to form active substance depots, followed by
a separating facility (230) for severing the carrier film web (10) into two or more sub-webs (15a, 15b, 15c, 15d) that at leat partially laterally engage with one another, and
an offset facility (240) designed to change the location of the sub-webs (15a, 15b, 15c, 15d) relative to each other such that none of the sub-webs laterally engages one of the other sub-webs; and
means for displacing the individual sub-webs (15a, 15b, 15c, 15d) relative to each other in the web direction (l) of the coated carrier film web (10) such that crosswise to the web direction active substance depots (12) have no offset (Al) to each other in the web direction; and
a cross cutting facility for severing the sub-webs in straight lines such that individual portions are obtained each containing only one active substance depot.

22. The device according to claim 21, wherein the offset facility (240) for enlarging the distance between the sub-webs (15a, 15b, 15c, 15d) comprises means for extending the transverse extension of two regions (11) arranged next adjacent on immediately adjacent sub-webs intended to form active substance depots (12) is equal or greater than the sum of the individual transverse extensions of these regions.

23. The device according to claim 22, wherein the offset facility (240) for enlarging the distance between the sub-webs (15a, 15b, 15c, 15d) has at least one swivel frame to laterally offset a sub-web to the web direction (l).

24. The device according to claim 21, wherein the contouring facility (210) is further designed for placing the active substance depots within regions (11) intended to form active substance depots (12) with geometries such that the minimum distance of the geometries to a rim boundary of the regions (11) corresponds to a predetermined value of 10 mm or less.

25. The device according to claim 21, further having a weeding facility (220) designed to remove the proportions (13) of the regions (11) not forming the active substance depots (12).

* * * * *